United States Patent [19]

Norling et al.

[11] 4,364,731

[45] Dec. 21, 1982

[54] METHODS FOR PRODUCING ADHESIVE BONDS BETWEEN SUBSTRATE AND POLYMER EMPLOYING AN INTERMEDIATE OXIDE LAYER

[75] Inventors: Barry K. Norling; James L. Bugg, Jr., both of San Antonio, Tex.

[73] Assignee: Board of Regents, The University of Texas System, Austin, Tex.

[21] Appl. No.: 229,752

[22] Filed: Jan. 29, 1981

[51] Int. Cl.$^3$ ............................ A61C 5/08; A61C 5/10
[52] U.S. Cl. ................................. 433/218; 204/192 C; 427/387; 427/407.1; 427/409; 427/412.1; 427/419.2; 428/446; 428/447; 428/448; 428/451; 428/428; 428/688; 428/432; 428/457; 433/212; 433/222; 433/223
[58] Field of Search ............... 428/457, 447, 448, 451, 428/446, 472, 688, 432, 428; 433/222, 223, 212, 218; 264/19; 523/109; 427/387, 407.1, 409, 412.1, 419.2; 204/192 C

[56] References Cited

U.S. PATENT DOCUMENTS

| | | | |
|---|---|---|---|
| T954,010 | 1/1977 | Brunner et al. | 427/335 |
| 3,079,361 | 2/1963 | Plueddemann | 260/40 |
| 3,306,800 | 2/1967 | Pluenddemann | 428/447 |
| 3,423,830 | 1/1969 | Halpern | 433/212 |
| 3,423,831 | 1/1969 | Semmelman | 433/212 |
| 3,508,983 | 4/1970 | Origer et al. | 156/3 |
| 3,522,075 | 7/1970 | Kiel | 428/447 |
| 3,644,166 | 2/1972 | Gause | 428/447 |
| 4,028,325 | 6/1977 | King | 433/218 |
| 4,052,524 | 10/1977 | Harakas et al. | 428/383 |
| 4,069,360 | 1/1978 | Yanagisawa et al. | 428/64 |
| 4,103,045 | 7/1978 | Lesaicherre et al. | 428/82 |
| 4,118,540 | 10/1978 | Amort et al. | 428/447 |

OTHER PUBLICATIONS

Johnson, K. R., "Restorations for Bottle-Mouth Syndrome and Fractured Anterior Teeth", *Dental Survey* pp. 30-33 (Jan. 1980).

*Primary Examiner*—Ellis P. Robinson
*Attorney, Agent, or Firm*—Arnold, White & Durkee

[57] ABSTRACT

Methods and compositions are provided for enhancing the bonding of polymeric materials to substrates via silane coupling agents. The methods involve depositing an oxide layer, such as alumina or silica, to a substrate, for example stainless steel. Next a silane coupling agent is applied which forms a strong chemical bond with the oxide layer. This layer is then coated or contacted with a polymeric substance. The resulting composite provides a strong adhesive bonding of substrate to polymer.

13 Claims, No Drawings

METHODS FOR PRODUCING ADHESIVE BONDS BETWEEN SUBSTRATE AND POLYMER EMPLOYING AN INTERMEDIATE OXIDE LAYER

BACKGROUND OF THE INVENTION

This invention relates generally to methods for producing adhesive bonds between a substrate and a polymer. More particularly the methods of this invention relate to enhancing the silane coupling bond between a substrate and polymer. Furthermore, the methods of the invention are especially suited for dental application in the restoration of teeth.

Heretofore the restoration of anterior teeth, particularly in children exhibiting decayed, eroded, or fractured anterior primary teeth, has involved fitting stainless steel crowns or caps over the damaged teeth. While the stainless steel crowns are well suited for structural and functional restoration of primary teeth, they are unaesthetic. For example, children fitted with such stainless steel crowns are often singled out by their peers as having "funny silver teeth". Aesthetic alternatives, however, principally the polycarbonate resin crowns, are not favored because such crowns exhibit poor wear resistance, inadequate retention, and susceptibility to cracking in service.

It therefore is a desirable approach to the restoration of teeth to combine the functional properties of the stainless steel crown with the aesthetics presented by the polymeric crowns. One such approach which has been suggested is to veneer the steel crown with a thin layer of polymeric resin. Although veneering has been successfully employed for a number of years for the restoration of natural teeth to mask defects such as developmental anomalies, and tetracycline and fluorosis stains, a durable stainless steel-polymer veneer has not been developed.

In veneering natural teeth, the damaged teeth are isolated, cleaned, etched with phosphoric acid, and dried. A composite restorative resin is applied to the etched surface and cured. Mechanical interlocking of the resin with the etched surface of the tooth enamel results in an adhesive bond strength which is sufficient to accomplish a restoration having acceptable clinical durability. Unfortunately, stainless steel is not amenable to a similar approach because retentive etch pits cannot be adequately developed in steel by acid etching.

Alternative approaches to produce a durable stainless steel-polymer veneer crown have involved chemical bonding techniques. The widely used industrial adhesive agents such as epoxy resins, phenol-formaldehyde resins and acrylic resins have been employed in the past to adhere polymers to substrates. Unfortunately the secondary chemical bonds formed between the substrate and polymer provide weak structural construction relative to the structural stresses presented to the crowns when in service. Not only are the veneered products subject to cracking, flaking and fracture, the veener composite may exhibit undesirable permeability to gases such as water vapor, and liquids, thereby allowing further weakening of the veneer structure.

Other approaches to combine functional strength and aesthetics include pigmenting the steel crowns. For example, commercial crowns were at one time available with white pigmented layers. These crowns, however, were not successful because of the rapid loss of the pigment coating after oral placement.

A more recent attempt to produce an aesthetic-functional composite involves a two-step chairside procedure. First the damaged tooth is sized with a stainless steel crown. Next the sized crown is removed and then subjected to laboratory treatment to construct a porcelain coating. Although a structurally and aesthetically durable crown is achieved, these merits must be weighed against the disadvantages of additional laboratory costs to produce a porcelain coating compared to a polymeric coating, and extended chair time.

As can be appreciated from the foregoing, the need still remains for a dental crown which combines the structural strength of steel and the aesthetics of a polymer resin. It is therefore a feature of the present invention to provide a methods for producing strong adhesive bonds between a substrate and polymer resin.

SUMMARY OF THE INVENTION

According to the present invention, methods are provided to enhance the adhesive bonding properties between a wide variety of polymeric materials and substrates. In one envisioned application, this invention is useful in the manufacture of dental crowns which exhibit the underlying structural strength of steel coupled with the cosmetic exterior of a dental polymeric resin.

The invention provides methods whereby enhanced adhesion between a polymeric material and substrate is achieved by the deposition of an intermediate layer of inorganic oxide onto a cleaned substrate surface, prior to the application of a layer of silane coupling agent. The principal novel feature of the invention is the application of an exogenous coating of inorganic oxide to which silane coupling agents bond well. It is this oxide layer on the substrate that provides a foothold for the adhesive bond of the silane coupling agent.

While silane coupling agents are extremely effective in bonding polymer resins to selected substrates, principally siliceous minerals, silane coupling agents alone are generally ineffective in producing usable bond adhesions between polymers and metallic substrates and between polymers and non-siliceous, non-metallic substrates. By tenaciously adhering an inorganic oxide coating to substrate surfaces as envisioned by the present invention, the substrates are rendered capable of developing adhesive bonds to polymeric resins through silane coupling agents.

Embodiments of the invention are discussed wherein various types of substrates and inorganic oxide coatings are employed. Also, composition embodiments are presented representing particular applications of the inventive process.

DETAILED DESCRIPTION OF PREFERRED EMBODIMENTS

The following discussion is in terms of the preferred embodiments of the invention, which represent the best mode known to the inventors at the time of this application.

In accordance with the preferred embodiments of this invention, a substrate such as a dental crown is provided having a surface cleaned of grease and other surface contaminants. Suitable substrate materials include metallic, ceramic, and polymeric substances. Surface preparation and cleaning may be accomplished by a variety of methods known in the art, for example, detergent baths, acid or caustic baths, ultrasonic vibration baths, and alcohol washes.

Further in accordance with such embodiments, the substrate surface is coated with a thin coating of an inorganic oxide. Desirably a submicron layer is deposited onto the substrate surface. The thickness of the coating should be sufficient so as to avoid substantial removal of the coating during further processing and handling; but desirably the coating should be as thin as possible to minimize weakening of the total composite through a fracture of the oxide layer.

It is evidently important to minimize stresses in the deposited oxide layer to prevent intra-layer failure as limiting overall bond strength. By limiting the thickness of the oxide coating, interlayer stress is effectively controlled. The oxide coating need be only thick enough to ensure complete coverage; theoretically a few angstroms, especially if the substrate is quite smooth. If handling operations between application of the oxide coating and application of the coupling agent and polymer cannot be avoided, a thicker coating may be required to avoid abrading the coating. In such cases, the coating may be applied thicker without seriously degrading bond strength provided measures are taken to ensure the oxide layer is deposited as stress-free as possible. In the case of sputter deposition, stress in the deposit is minimized by controlling the temperature of the substrate and by biasing the substrate during deposition. The precise methods and operating parameters for producing a stress free coating are strongly dependent on the material and particular design of the apparatus used for the depositions. However, the techniques of temperature control and bias sputtering, and the methods for optimizing the techniques for producing minimal stress deposits for any given material, are well known to those skilled in the art.

For applications subject to no substantial amount of abuse to the coating prior to silane and polymeric application, an oxide coating much less than one micrometer is preferred, and coatings of a few hundred angstroms have proven effective.

Suitable exogenous inorganic oxides include in particular alumina, silica, aluminate, silicate, aluminosilicate compounds and silica-rich glasses. Silica however is preferred. Deposits of these oxides can be accomplished by a variety of methods such as sputter coating, chemical vapor deposition, activated reactive vapor depositions and reactive ion plating. Sputter deposition, in particular, readily develops a dense, adherent oxide coating of controllable, low film thickness.

Further in accordance with the preferred embodiments of the invention, the oxide coating is next layered with a dilute silane coupling agent solution. Application of the silane agent may be achieved by swabbing, wiping, dipping, painting, spraying or any other technique which deposits a thin uniform layer of fluid film. The silane coupling layer may desirably be any of a variety of organo-silane agents already widely used and commercially available such as those employed for coupling glass fibers and particulate mineral fillers to a resin matrix for the purpose of making a mineral reinforced polymer. The selection of the silane coupling agent to achieve optimum coupling for a chosen polymer-substrate system follows the same principles used by those skilled in the art for choosing the coupling agent for a particulate or filamentous filler. Exemplary silane coupling agents include but are not limited to Dow Corning Z-6032, styrylamine functional silane, gamma-aminopropyl triethoxysilane, and vinyl trichlorosilane.

Immediately after the adhesive silane coupling agent has been applied, the polymer is applied over the silane coated surface by molding, extruding, calendering, painting, or dipping. If necessary, the composite structure is allowed to cure, thereby enhancing structural stability and integrity. The polymeric materials whose adhesion to the substrate is improved by the methods of this invention include, for example, epoxy-resins, urethane resins, vinyl esters, rubber latex, and acrylic resins.

Alternatively, the silane coupling agent may be incorporated directly into the resin prior to its application to the oxide coated substrate. While this particular embodiment may not produce as effective bonding strengths as the direct application of silane to the oxide coating, it has the economic advantage of eliminating a processing step while the patient is chairside. This combination has been used successfully with polymers filled with particulate or fibrous materials.

To further illustrate the invention, Applicants have performed several laboratory experiments which have yielded good results in providing a structurally sound and durable veneer composite. The examples which follow, which should not be considered as limiting the invention but rather only as exemplary of various embodiments, are based on those laboratory results.

In the following examples the materials and apparatus were obtained from the following manufacturers:

| Description | Manufacturer |
| --- | --- |
| Sputtering apparatus:<br>Model 7375 triple 6-inch planar magnetron radio-frequency sputtering apparatus | Vacuum Technology Associates<br>Boulder, Colorado |
| Sputtering targets:<br>(6" diameter by ¼" thick)<br>Alumina, 99.8% high density recrystallized | Coors Porcelain Company<br>Boulder, Colorado |
| Silica, 99.98% fused quartz (transparent) | Quartz Scientific, Inc.<br>Fairport Harbor, Ohio |
| Silane coupling agents:<br>Z-6032, N—beta-(N—vinylbenzylamino) ethyl-gamma-aminopropyl-trimethoxy silane, supplied as 40% solution in methanol | Dow Corning Corporation<br>Midland, Michigan |
| Dental composite resins:<br>Cervident | Pennwalt S.S. White<br>Philadelphia, Pennsylvania |
| Vytol, Nuva-Seal P.A., Nuva-Fil P.A. | L.D. Caulk Company<br>Milford, Delaware |
| Enamelite 500 | Lee Pharmaceuticals<br>So. El Monte, California |
| Amoco Super-C | American Consolidated Manufacturing Co.<br>Philadelphia, Pennsylvania |
| Bead blasting apparatus:<br>Trinco Dry Blast, model 24/BP | Trinity Tool Company<br>Warren, Michigan |
| Abrasive agents:<br>Dental diamond point, Densco 3LCX | Teledyne Densco<br>Denver, Colorado |
| Aluminum oxide cylinder, Ticonium 201W | Ticonium<br>Albany, New York |
| Silicon carbide abrasive paper, 320 mesh, adhesive backed | Buehler Ltd.<br>Evanston, Illinois |

EXAMPLE I

Stainless steel pedodontic anterior crowns, commercially available from Unitek Corporation, Monrovia, Calif., were ultrasonically cleaned in an alkaline detergent solution (Sparkleen, Fisher Scientific, Pittsburg, Pa.) for 30 minutes, rinsed with deionized water and dried at 100° C. The crowns were placed in the sputtering apparatus, Model 7375 triple 6-inch planar magnetron radio-frequency sputtering apparatus manufactured by Vacuum Technology Associates, Boulder, Colo. Sputter etching proceeded for 10 minutes in argon. Silica, 99.98% fused quartz obtained from Quartz Scientific, Inc., Fairport Harbor, Ohio, was then deposited for 2 minutes at 500 Watts (W) in 95% argon, 5% oxygen atmosphere at 1 micron pressure. The crowns were then crimped and trimmed as usual to adapt them to the individual teeth, then cleaned in alkaline detergent and rinsed. A 2% methanolic solution of Z-6032, N-beta-(N-vinylbenzylamino) ethyl-gamma-aminopropyltrimethoxysilane, supplied as a 40% methanolic solution by Dow Corning Corporation, Midland, Mich., was applied with a cotton swab and allowed to dry. Nuvafil opaquer, marketed by L. D. Caulk Company, Milford, Del., was applied to the labial surface and cured by exposure to the ultraviolet light (Nuva-Light) followed by a similar application of translucent Nuva-Fil. The crowns were cemented into place according to standard procedures.

Pedodontic crowns made accordingly have been in service for over a year in actual patients.

EXAMPLES II-V

Type 305 stainless steel sheet stock, obtained from Unitek Corporation, was mounted and subjected to various surface treatments involving application of exogenous oxide coating. Table I presents data which demonstrates that the improved bonding of the polymer resin results from the combination of oxide treatment and silane coupling agent rather than each independently. An untreated control subjected to no oxide or silane treatment is included for comparison. In each instance the polymer bound to the substrate was Enamelite 500 marketed by Lee Pharmaceuticals, S. El Monte, Calif. To assess the resultant bonding strength between the polymer resin and substrate, cylinders of composite Enamelite 500 resin were cured against the steel surface. The sample composites were then soaked for 24 hours in artificial saliva, a dilute aqueous solution of various electrolytes. Shear bond strengths were determined in an Instron Universal testing machine.

TABLE 1

Shear Bond Strengths Demonstrating that Improved Bond Strength Results From Combination of Silica and Silane Rather than Each Separately

| Example | Siliceous Layer | Silane | Average Shear Bond Strength |
|---|---|---|---|
| II | None | None | 348 psi |
| III | Sputtered silica (2 min, 500W, 95 Ar/5O$_2$ at 1 micron) | None | 325 psi |
| IV | None | 2% Methanolic Solution of Z-6032 | 201 psi |
| V | Sputtered silica (2 min, 500W, 95 Ar/5O$_2$ at 1 micron) | 2% Methanolic Solution of Z-6032 | 1489 psi |

EXAMPLES VI-XV

A series of experiments were performed to demonstrate the effects of surface roughening procedures, which are common means of increasing bond strength, and sputter deposited alumina and silica. Enamelite 500 was the bonded polymeric resin. While silica is clearly a superior coating for the substrate, as might be expected when bonding with the silicon based silane coupling agent, the data also indicates that the deposited coating thickness is a variable in the resultant bonding strength. The thickness of the oxide deposit may be controlled by limiting the exposure time to sputter treatment.

TABLE 2

Comparison of Surface Treatments of 305 Stainless Steel Sheet Stock for Adhesion to Dental Composite Resin

| Sample | Surface Treatment | Silane | Average Shear Bond Strength |
|---|---|---|---|
| VI | Alkaline cleaned only | 2% Methanolic Solution of Z-6032 | 328 psi |
| VII | Polished | 5% Methanolic Solution of Z-6032 | 202 psi |
| VIII | Bead blasted | None | 307 psi |
| IX | Roughened with Aluminum Oxide Stone | None | 361 psi |
| X | Roughened with SiC Paper | None | 371 psi |
| XI | Roughened with Diamond Stone | None | 600 psi |
| XII | Polished Plus Sputtered Alumina (10 min, 500W, 95 Ar/5 O$_2$ at 1 micron) | 5% Methanolic Solution of Z-6032 | 458 psi |
| XIII | Polished Plus Sputtered Alumina (2 min, 500W, 95 Ar/5 O$_2$ at 1 micron) | 5% Methanolic Solution of Z-6032 | 706 psi |
| XIV | Polished Plus Sputtered Silica (10 min, 500W 95 Ar/5 O$_2$ at 1 micron) | 5% Methanolic Solution of Z-6032 | 683 psi |
| XV | Polished Plus Sputtered Silica (2 min, 500W, 95 Ar/5 O$_2$ at 1 micron) | 5% Methanolic Solution of Z-6032 | 1250 Psi |

EXAMPLES XVI-XXI

Table 3 demonstrates the effect of varying the concentration of silane in the methanolic solution which is applied to the sputtered silica layer prior to applying the resin. For this particular combination of silane and solvent (Z-6032 and methanol), the optimum concentration was 2%. For most silane coupling agents, the desirable concentration ranges from about 0.1 to about 10% with the optimum lying in the range from about 0.5 to about 5.0%. The solvent selected for dissolution of the coupling agent should preferably be compatible or unreactive with the silane coupling agent and compatible with the substrate coating. The solvent selected should also have a suitable evaporation rate to facilitate uniform coating and adequate curing rates.

TABLE 3

Effect of Silane Coupling Agent Concentration on Bond Strength of Enamelite 500 to Silica Coated on 305 Stainless Steel (2 min, 500W, 95 Ar/5 O$_2$ 1 micron)

| Example | Silane Coupling Agent | Average Shear Bond Strenght |
|---|---|---|
| XVI | None | 325 psi |
| XVII | 0.5% Methanolic Solution of Z-6032 | 1051 psi |
| XVIII | 1.0% Methanolic Solution of Z-6032 | 1308 psi |
| XIX | 2.0% Methanolic Solution of Z-6032 | 1489 psi |

TABLE 3-continued

Effect of Silane Coupling Agent
Concentration on Bond Strength of Enamelite 500
to Silica Coated on 305 Stainless Steel
(2 min, 500W, 95 Ar/5 O$_2$ 1 micron)

| Example | Silane Coupling Agent | Average Shear Bond Strenght |
|---------|----------------------|----------------------------|
| XX | 5.0% Methanolic Solution of Z-6032 | 1250 psi |
| XXI | 10.0% Methanolic Solution of Z-6032 | 973 psi |

EXAMPLES XXII–XXVII

Various commercially available polymeric resins were tested according to the methods of this invention as described in Example I. All resins listed are dental composite resin filling material. All have matrix resins based on aromatic dimethacrylate except the last, Super C, which is based on methyl methacrylate.

TABLE 4

Resultant Bond Strengths, 305
Stainless Steel Sheet stock to Various Polymers

| | | | | Average Shear Bond Strength |
|---|---|---|---|---|
| XXII | Sputtered Silica (2 min, 500W, 95 Ar/5 O$_2$ at 1 micron) | 2% Methanolic Solution of Z-6032 | Cervident | 664 psi |
| XXIII | Sputtered Silica (2 min, 500W, 95 Ar/5 O$_2$ at 1 micron) | 2% Methanolic Solution of Z-6032 | Vytol | 1138 psi |
| XXIV | Sputtered Silica (2 min, 500W, 95 Ar/5 O$_2$ at 1 micron) | 2% Methanolic Solution of Z-6032 | Nuvaseal | 1480 psi |
| XXV | Sputtered Silica (2 min, 500W, 95 Ar/5 O$_2$ at 1 micron) | 2% Methanolic Solution of Z-6032 | Enamelite 500 | 1489 psi |
| XXVI | Sputtered Silica (2 min, 500W, 95 Ar/5 O$_2$ at 1 micron) | 2% Methanolic Solution of Z-6032 | Nuvafil | 1567 psi |
| XXVII | Sputtered Silica (2 min, 500W, 95 Ar/5 O$_2$ at 1 micron) | 2% Methanolic Solution of Z-6032 | Super C | 2300 psi |

As can readily be appreciated from the foregoing examples, the deposition of an inorganic oxide, especially aluminum oxides and silicon oxides, serve to enhance the silane bonding strengths between substrate and polymer layers. Further the techniques of this invention may be applied to substrates other than metallic substrates. Ceramic and polymeric substrates are also amenable to the described oxide deposition step. Sputtering for example is virtually a universally applicable means of applying an oxide coating to any class of substrate. Each substrate however may require some adjustments of the sputtering parameters. For example, for some polymer substrates it may be highly desirable to sputter etch the substrate in oxygen or argon/oxygen prior to sputter depositions of the oxide. However, the techniques for sputter etching substrates and the parameters for obtaining adherent oxide coating are known to those skilled in the art of sputter deposition.

Similarly, the choice of polymer coating may be varied according to desire and particular end uses. While the silane coupling agent forms an adhesive bond which is most effective when adhering thermosetting polymers (e.g. epoxies, phenolics, diallyls, and urea-formaldehydes), selection of an appropriate silane coupling agent also enhances substrate bonding to thermoplastic resin polymers such as nylon, polycarbonate, and polyacetal. The general guidelines for selection of a coupling agent for any given polymer system are well known and available in brochures from silane coupling agent manufacturers.

UTILITY

As illustrated in Example I the methods and compositions of the invention are useful in preparation of dental crowns which incorporate the functional strength of steel substrate and the aesthetics of toothlike enamel from the polymer coating. The same dual functionalities provided by the methods of this invention also apply to the application of aesthetic coatings to orthodontic brackets, bands and wires.

Further the methods of this invention may be applied to the semiconductor packaging industry. Traditionally, semiconductor devices have been marketed in a variety of packages depending on the severity of the environment to be encountered in the end application. For the most severe applications requiring total hermeticity, the packages are either metal with glass to metal seals wherever leads penetrate the package or ceramic with "solder-glass" seals between package components and at lead penetrations. By such means packages are created offering environmental isolation sufficient for the most demanding applications, e.g., military and aerospace applications. As the technology of device fabrication has progressed, the cost of the active circuit chips has fallen to the point where the cost of the exotic hermetic packaging may constitute most of the cost of the ultimate device. Less costly alternative packaging usually consists of a transfer molded plastic package. These epoxy, silicone or epoxy-silicone resin packages will not meet the stringent requirements for hermeticity partly because the lead-package junction is not sufficiently "tight" to prevent migration of gasses (including water vapor) into the package. The resulting lack of hermeticity leads to decreased product reliability.

The packaging problem is normally met by offering the same device (e.g., integrated circuit) in two or more package configurations so that the cost of the hermetic package is incurred wherever the application merits the increased reliability while the lower priced package may be used wherever the reduced reliability may be acceptably traded for lower initial price (e.g., consumer electronics).

According to the methods of this invention, an inexpensive plastic package with improved hermeticity may be achieved by coating the semiconductor leads with silica and silane prior to encapsulating in plastic.

Although the invention has been described in terms of particular embodiments which Applicant believes to represent the best modes of the invention at the time of this application, it will be recognized by those skilled in the art that various changes may be made in the composition and method embodiments of this specification without departing from the scope of the invention as defined in the following claims.

What is claimed is:

1. A method for producing a dental crown composite comprising the steps of:
   (a) providing a clean dental crown substrate surface;

(b) depositing onto the substrate surface an exogenous coating of inorganic oxide to a desired thickness on the substrate surface to enhance adhesion between the substrate and subsequently applied silane coupling agent;

(c) bonding a layer of silane coupling agent to the oxide coating; and (d) applying a polymeric resin to the exposed silane coupling layer.

2. The method according to claim 1 wherein the exogenous inorganic metal oxide coating is selected from the group consisting of alumina, silica, aluminates, silicates, alumino-silicates, and silica-rich glasses.

3. The method according to claim 1 wherein the exogenous inorganic metal oxide coating is alumina or silica.

4. The method according to claim 1 wherein the dental crown substrate is selected from the group consisting of metallic, ceramic, and polymeric materials.

5. The method according to claim 1 wherein the substrate is a metallic material.

6. The method according to claim 1 wherein the substrate is stainless steel.

7. The method according to claim 1 wherein the oxide coating is deposited by sputter deposition.

8. A dental crown composite comprising
a dental crown substrate;
a layer of exogenous inorganic oxide applied to a desired thickness to the surface of the substrate
a layer of silane coupling agent bonded to the layer of oxide; and
a coating of polymeric resin applied to the surface of the silane coupling layer.

9. The dental crown composite according to claim 8 wherein the exogenous oxide is selected from the group consisting of alumina, silica, aluminate, silicates, alumino-silicates and silica-rich glasses.

10. The dental crown composite according to claim 8 wherein the exogenous oxide is alumina or silica.

11. The dental crown composite according to claim 8 wherein the dental crown substrate is selected from the group consisting of metallic, ceramic and polymeric materials.

12. The dental crown composite of claim 8 wherein the substrate is a metallic material.

13. The dental crown composite of claim 8 wherein the substrate is stainless steel.

* * * * *